US008183221B2

(12) United States Patent (10) Patent No.: US 8,183,221 B2
Thakker et al. (45) Date of Patent: May 22, 2012

(54) SUPPRESSION OF SCN9A GENE EXPRESSION AND/OR FUNCTION FOR THE TREATMENT OF PAIN

(75) Inventors: Deepak Thakker, Blaine, MN (US); Eric Burright, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 42 days.

(21) Appl. No.: 12/676,596

(22) PCT Filed: Sep. 5, 2008

(86) PCT No.: PCT/US2008/075409
§ 371 (c)(1),
(2), (4) Date: Jun. 4, 2010

(87) PCT Pub. No.: WO2009/033027
PCT Pub. Date: Mar. 12, 2009

(65) Prior Publication Data
US 2010/0273857 A1 Oct. 28, 2010

Related U.S. Application Data

(60) Provisional application No. 60/970,196, filed on Sep. 5, 2007.

(51) Int. Cl.
*A61K 48/00* (2006.01)
*C07H 21/04* (2006.01)
*C12N 15/63* (2006.01)

(52) U.S. Cl. ... 514/44; 536/23.1; 536/24.31; 536/24.33; 536/24.5; 435/320.1

(58) Field of Classification Search .................... None
See application file for complete search history.

(56) References Cited

U.S. PATENT DOCUMENTS

| | | | |
|---|---|---|---|
| 5,334,711 A | 8/1994 | Sproat et al. |
| 5,350,674 A | 9/1994 | Boenisch et al. |
| 5,585,362 A | 12/1996 | Wilson et al. |
| 5,627,053 A | 5/1997 | Usman et al. |
| 5,716,824 A | 2/1998 | Beigelman et al. |
| 5,849,902 A | 12/1998 | Arrow et al. |
| 5,914,131 A | 6/1999 | Merrill et al. |
| 5,989,912 A | 11/1999 | Arrow et al. |
| 6,506,559 B1 | 1/2003 | Fire et al. |
| 6,617,438 B1 | 9/2003 | Beigelman et al. |
| 7,101,995 B2 | 9/2006 | Lewis et al. |
| 7,148,342 B2 | 12/2006 | Tolentino et al. |
| 7,173,015 B2 | 2/2007 | Schreiber et al. |
| 7,235,654 B2 | 6/2007 | Li et al. |
| 7,241,618 B2 | 7/2007 | Agami et al. |
| 7,294,504 B1 | 11/2007 | Wang |
| 7,345,027 B2 | 3/2008 | Tolentino et al. |
| 7,399,586 B2 | 7/2008 | Klinghoffer et al. |
| 2002/0119440 A1 | 8/2002 | Akiba et al. |
| 2003/0022813 A1 | 1/2003 | Chaplan et al. |
| 2005/0064489 A1 | 3/2005 | Zhang et al. |
| 2005/0095246 A1 | 5/2005 | Shafer |
| 2006/0128644 A1 | 6/2006 | Barclay et al. |
| 2006/0178328 A1* | 8/2006 | Kaemmerer .................... 514/44 |
| 2008/0200420 A1 | 8/2008 | Zamore et al. |

FOREIGN PATENT DOCUMENTS

| | | |
|---|---|---|
| WO | 91/19813 A1 | 12/1991 |
| WO | 92/07065 A1 | 4/1992 |
| WO | 93/15187 A1 | 8/1993 |
| WO | 97/26270 A2 | 7/1997 |
| WO | 98/08856 A2 | 3/1998 |
| WO | 98/13526 A1 | 4/1998 |
| WO | 99/32619 A1 | 7/1999 |
| WO | 00/44895 A1 | 8/2000 |
| WO | 01/75164 A2 | 10/2001 |
| WO | 02/36747 A2 | 10/2001 |
| WO | 02/44321 A2 | 6/2002 |
| WO | 03/070897 A2 | 8/2003 |
| WO | 03/087769 A2 | 11/2003 |
| WO | 2006/047687 A | 5/2006 |
| WO | 2007/109324 A | 9/2007 |

OTHER PUBLICATIONS

Scherer et al. (Nat. Biotechnol., 2003, 21(12), pp. 1457-1465).*
Zhang et al. (Current Pharmaceutical Biotechnology 2004, vol. 5, p. 1-7).*
Bertrand et al. (Biochemical and Biophysical Research Communications, 296, 2002, 1000-1004).*
Ahmad et al. "A Stop Codon Mutation in SCN9A Causes Lack of Pain Sensation." Human Molecular Genetics, 2007, vol. 16, No. 17, pp. 2114-2121.
Altier et al. "Differential Role of N-Type Calcium Channel Splice Isoforms in Pain." The Journal of Neuroscience, Jun. 13, 2007, 27(24):6363-6373.
Cantin et al. "Entry Granted." Nature, vol. 448, Jul. 5, 2007.
Cox et al. "An SCN9A Channelopathy Causes Congenital Inability to Experience Pain." Nature, vol. 444, Dec. 14, 2006.
Crombez et al. "A Non-Covalent Peptide-Based Strategy for siRNA Delivery." Biochemical Society Transactions, 2007, vol. 35, Part 1.
D'Arcangelo et al. "Neuronal Growth Factor Regulation of Two Different Sodium Channel Types Through Distinct Signal Transduction Pathways." The Journal of Cell Biology, vol. 122, No. 4, Aug. 1993, pp. 915-921.
Dong et al. "Small Interfering RNA-Mediated Selective Knockdown of Nav1.8 Tetrodotoxin-Resistant Sodium Channel Reverses Mechanical Allodynia in Neuropathic Rats." Neuroscience 146, 2007, pp. 812-821.
Dykxhoorn et al. "Knocking Down Disease with siRNAs." Cell 126, Jul. 28, 2006.

(Continued)

*Primary Examiner* — Amy Bowman

(57) ABSTRACT

Disclosed herein are methods, sequences and nucleic acid molecules used to treat pain. Specifically, the methods and sequences include locally administering molecules that suppress the expression of amino acid sequences that encode for $Na_v1.7$ channels or that otherwise inhibit the function of $Na_v1.7$ channels. Local suppression of $Na_v1.7$ channel levels and/or function will occur in the peripheral sensory neurons of the dorsal root ganglia.

5 Claims, 2 Drawing Sheets

OTHER PUBLICATIONS

Hoyt et al. "Discovery of a Novel Class of Benzazepinone Nav1.7 Blockers: Potential Treatments for Neuropathic Pain." Bioorganic & Medicinal Chemistry Letters 17, 2007, pp. 4630-4634.

Kim et al. "Strategies for Silencing Human Disease Using RNA Interference." Nature Reviews. vol. 8, Mar. 2007.

Nassar et al. "Nociceptor-Specific Gene Deletion Reveals a Major Role for Nav1.7 (PN1) in Acute and Inflammatory Pain." PNAS, vol. 101, No. 34, Aug. 24, 2004, pp. 12706-12711.

Oliveira et al. "Targeted Delivery of siRNA." Journal of Biomedicine and Biotechnology, vol. 2006, pp. 1-9.

Raymond et al. "Expression of Alternatively Spliced Sodium Channel a-Subunit Genes." The Journal of Biological Chemistry, vol. 279, No. 44, Oct. 2004, pp. 46234-46241.

Yeomans et al. "Decrease in Inflammatory Hyperalgesia by Herpes Vector-Mediated Knockdown of Nav1.7 Sodium Channels in Primary Afferents." Human Gene Therapy 16:271-277 (Feb. 2005.

* cited by examiner

Figure 3A
Figure 3B
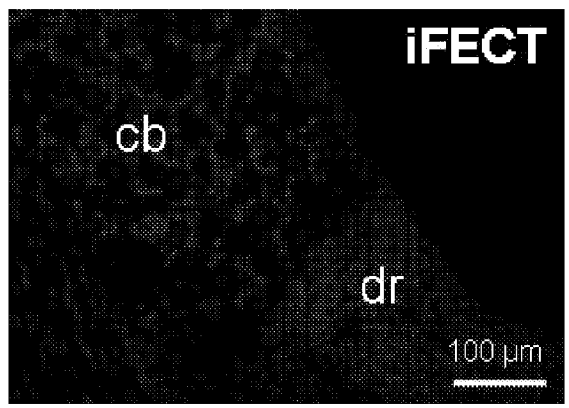
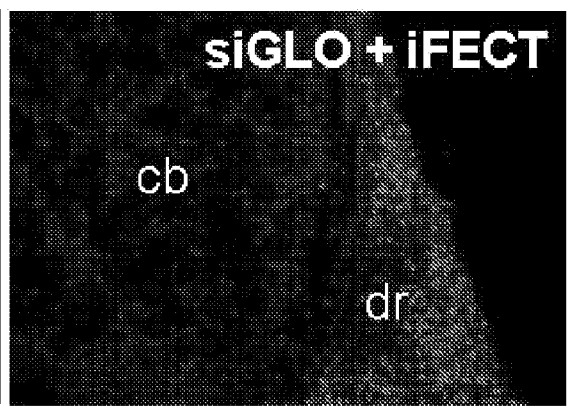

SEQUENCE LISTING

```
<160> NUMBER OF SEQ ID NOS: 61

<210> SEQ ID NO 1
<211> LENGTH: 19
<212> TYPE: DNA
<213> ORGANISM: Rattus sp.

<400> SEQUENCE: 1
gggaatcaat tacgtgaaa                                                    19

<210> SEQ ID NO 2
<211> LENGTH: 19
<212> TYPE: DNA
<213> ORGANISM: Rattus sp.

<400> SEQUENCE: 2
cattaaatct ctacggaca                                                    19

<210> SEQ ID NO 3
<211> LENGTH: 19
<212> TYPE: DNA
<213> ORGANISM: Rattus sp.

<400> SEQUENCE: 3
aggaagaagc tgaggcgat                                                    19

<210> SEQ ID NO 4
<211> LENGTH: 19
<212> TYPE: DNA
<213> ORGANISM: Rattus sp.

<400> SEQUENCE: 4
gaggaaagca tccgaaaga                                                    19

<210> SEQ ID NO 5
<211> LENGTH: 19
<212> TYPE: DNA
<213> ORGANISM: Homo sapiens
```

```
<400> SEQUENCE: 5
cagaagaaca gaagaaata                                               19

<210> SEQ ID NO 6
<211> LENGTH: 19
<212> TYPE: DNA
<213> ORGANISM: Homo sapiens

<400> SEQUENCE: 6
tgaagaagct aaacagaaa                                               19

<210> SEQ ID NO 7
<211> LENGTH: 19
<212> TYPE: DNA
<213> ORGANISM: Homo sapiens

<400> SEQUENCE: 7
ggtaagagct acaaagaat                                               19

<210> SEQ ID NO 8
<211> LENGTH: 19
<212> TYPE: DNA
<213> ORGANISM: Homo sapiens

<400> SEQUENCE: 8
aggcagagga agagatata                                               19

<210> SEQ ID NO 9
<211> LENGTH: 19
<212> TYPE: DNA
<213> ORGANISM: Homo sapiens

<400> SEQUENCE: 9
agacagagat gatgattta                                               19

<210> SEQ ID NO 10
<211> LENGTH: 19
<212> TYPE: DNA
<213> ORGANISM: Homo sapiens

<400> SEQUENCE: 10
gggaaagaca gcaaggaaa                                               19

<210> SEQ ID NO 11
<211> LENGTH: 19
<212> TYPE: DNA
<213> ORGANISM: Homo sapiens

<400> SEQUENCE: 11
gaacaagaca gaacagaaa                                               19

<210> SEQ ID NO 12
<211> LENGTH: 19
<212> TYPE: DNA
<213> ORGANISM: Homo sapiens

<400> SEQUENCE: 12
gtgaagaaga ctttagaaa                                               19

<210> SEQ ID NO 13
<211> LENGTH: 19
<212> TYPE: DNA
<213> ORGANISM: Homo sapiens
```

```
<400> SEQUENCE: 13
ccaaagattt ccagggaga                                               19

<210> SEQ ID NO 14
<211> LENGTH: 19
<212> TYPE: DNA
<213> ORGANISM: Homo sapiens

<400> SEQUENCE: 14
taacatagag tcagggaaa                                               19

<210> SEQ ID NO 15
<211> LENGTH: 19
<212> TYPE: DNA
<213> ORGANISM: Homo sapiens

<400> SEQUENCE: 15
gaaagaagaa acagaagaa                                               19

<210> SEQ ID NO 16
<211> LENGTH: 19
<212> TYPE: DNA
<213> ORGANISM: Homo sapiens

<400> SEQUENCE: 16
ggagataaga caagcagaa                                               19

<210> SEQ ID NO 17
<211> LENGTH: 19
<212> TYPE: DNA
<213> ORGANISM: Homo sapiens

<400> SEQUENCE: 17
ctgaatacta agaaggaaa                                               19

<210> SEQ ID NO 18
<211> LENGTH: 19
<212> TYPE: DNA
<213> ORGANISM: Homo sapiens

<400> SEQUENCE: 18
gagaagaagc agaggctga                                               19

<210> SEQ ID NO 19
<211> LENGTH: 19
<212> TYPE: DNA
<213> ORGANISM: Homo sapiens

<400> SEQUENCE: 19
gaaagatgat gatgaagaa                                               19

<210> SEQ ID NO 20
<211> LENGTH: 19
<212> TYPE: DNA
<213> ORGANISM: Homo sapiens

<400> SEQUENCE: 20
tgggaaacct gaagcataa                                               19

<210> SEQ ID NO 21
<211> LENGTH: 19
<212> TYPE: DNA
<213> ORGANISM: Homo sapiens
```

```
<400> SEQUENCE: 21
gaacacagtt ggtttgaaa                                               19

<210> SEQ ID NO 22
<211> LENGTH: 19
<212> TYPE: DNA
<213> ORGANISM: Homo sapiens

<400> SEQUENCE: 22
tgacagaaga acagaagaa                                               19

<210> SEQ ID NO 23
<211> LENGTH: 19
<212> TYPE: DNA
<213> ORGANISM: Homo sapiens

<400> SEQUENCE: 23
aagaagaagc tgaggcaat                                               19

<210> SEQ ID NO 24
<211> LENGTH: 19
<212> TYPE: DNA
<213> ORGANISM: Homo sapiens

<400> SEQUENCE: 24
tttcaaaggc agaggaaga                                               19

<210> SEQ ID NO 25
<211> LENGTH: 19
<212> TYPE: DNA
<213> ORGANISM: Homo sapiens

<400> SEQUENCE: 25
cttgaagagt ccagacaaa                                               19

<210> SEQ ID NO 26
<211> LENGTH: 19
<212> TYPE: DNA
<213> ORGANISM: Homo sapiens

<400> SEQUENCE: 26
gctaaagaaa gaagaaaca                                               19

<210> SEQ ID NO 27
<211> LENGTH: 19
<212> TYPE: DNA
<213> ORGANISM: Homo sapiens

<400> SEQUENCE: 27
agaagaaaca gaagaaaga                                               19

<210> SEQ ID NO 28
<211> LENGTH: 19
<212> TYPE: DNA
<213> ORGANISM: Homo sapiens

<400> SEQUENCE: 28
gctgagaaat tgtcgaaat                                               19

<210> SEQ ID NO 29
<211> LENGTH: 19
<212> TYPE: DNA
<213> ORGANISM: Homo sapiens
```

```
<400> SEQUENCE: 29
gagcaagcat attaacaaa                                                  19

<210> SEQ ID NO 30
<211> LENGTH: 19
<212> TYPE: DNA
<213> ORGANISM: Homo sapiens

<400> SEQUENCE: 30
cataaaagat ggagacaga                                                  19

<210> SEQ ID NO 31
<211> LENGTH: 19
<212> TYPE: DNA
<213> ORGANISM: Homo sapiens

<400> SEQUENCE: 31
taacaaagcc agacaaaga                                                  19

<210> SEQ ID NO 32
<211> LENGTH: 19
<212> TYPE: DNA
<213> ORGANISM: Homo sapiens

<400> SEQUENCE: 32
aaaggaagac aaagggaaa                                                  19

<210> SEQ ID NO 33
<211> LENGTH: 19
<212> TYPE: DNA
<213> ORGANISM: Homo sapiens

<400> SEQUENCE: 33
aaagggagat gctgagaaa                                                  19

<210> SEQ ID NO 34
<211> LENGTH: 19
<212> TYPE: DNA
<213> ORGANISM: Homo sapiens

<400> SEQUENCE: 34
taacaaacac tgtggaaga                                                  19

<210> SEQ ID NO 35
<211> LENGTH: 19
<212> TYPE: DNA
<213> ORGANISM: Homo sapiens

<400> SEQUENCE: 35
agtattgaac aaagggaaa                                                  19

<210> SEQ ID NO 36
<211> LENGTH: 19
<212> TYPE: DNA
<213> ORGANISM: Homo sapiens

<400> SEQUENCE: 36
aggcgaagca gcagaacaa                                                  19

<210> SEQ ID NO 37
<211> LENGTH: 19
<212> TYPE: DNA
<213> ORGANISM: Homo sapiens
```

```
<400> SEQUENCE: 37
tagcagatgt ggaaggatt                                                      19

<210> SEQ ID NO 38
<211> LENGTH: 19
<212> TYPE: DNA
<213> ORGANISM: Homo sapiens

<400> SEQUENCE: 38
aaacaaacct tacgtgaat                                                      19

<210> SEQ ID NO 39
<211> LENGTH: 19
<212> TYPE: DNA
<213> ORGANISM: Homo sapiens

<400> SEQUENCE: 39
aaatatgaat gctgaggaa                                                      19

<210> SEQ ID NO 40
<211> LENGTH: 19
<212> TYPE: DNA
<213> ORGANISM: Homo sapiens

<400> SEQUENCE: 40
ccaaagaaga aagaaaga                                                       19

<210> SEQ ID NO 41
<211> LENGTH: 19
<212> TYPE: DNA
<213> ORGANISM: Homo sapiens

<400> SEQUENCE: 41
ctgacaaact gcatattta                                                      19

<210> SEQ ID NO 42
<211> LENGTH: 19
<212> TYPE: DNA
<213> ORGANISM: Homo sapiens

<400> SEQUENCE: 42
agggagatgc tgagaaatt                                                      19

<210> SEQ ID NO 43
<211> LENGTH: 19
<212> TYPE: DNA
<213> ORGANISM: Homo sapiens

<400> SEQUENCE: 43
cattgaacat gctgattaa                                                      19

<210> SEQ ID NO 44
<211> LENGTH: 19
<212> TYPE: DNA
<213> ORGANISM: Homo sapiens

<400> SEQUENCE: 44
gcatgcagct ctttggtaa                                                      19

<210> SEQ ID NO 45
<211> LENGTH: 19
<212> TYPE: DNA
<213> ORGANISM: Homo sapiens
```

```
<400> SEQUENCE: 45
agacaatctt acagcaatt                                                19

<210> SEQ ID NO 46
<211> LENGTH: 19
<212> TYPE: DNA
<213> ORGANISM: Homo sapiens

<400> SEQUENCE: 46
aagaagaccc tgatgcaaa                                                19

<210> SEQ ID NO 47
<211> LENGTH: 19
<212> TYPE: DNA
<213> ORGANISM: Homo sapiens

<400> SEQUENCE: 47
ggaagacagt gatggtcaa                                                19

<210> SEQ ID NO 48
<211> LENGTH: 19
<212> TYPE: DNA
<213> ORGANISM: Homo sapiens

<400> SEQUENCE: 48
cagacaagat cttcactta                                                19

<210> SEQ ID NO 49
<211> LENGTH: 19
<212> TYPE: DNA
<213> ORGANISM: Homo sapiens

<400> SEQUENCE: 49
agccagacaa agagaaata                                                19

<210> SEQ ID NO 50
<211> LENGTH: 19
<212> TYPE: DNA
<213> ORGANISM: Homo sapiens

<400> SEQUENCE: 50
cttcgaactt tcagagtat                                                19

<210> SEQ ID NO 51
<211> LENGTH: 19
<212> TYPE: DNA
<213> ORGANISM: Homo sapiens

<400> SEQUENCE: 51
gagtagagca agcatatta                                                19

<210> SEQ ID NO 52
<211> LENGTH: 19
<212> TYPE: DNA
<213> ORGANISM: Homo sapiens

<400> SEQUENCE: 52
tgtacttgct ataggaaat                                                19

<210> SEQ ID NO 53
<211> LENGTH: 19
<212> TYPE: DNA
<213> ORGANISM: Homo sapiens
```

-continued

```
<400> SEQUENCE: 53
ggtcaagcta tgtgcctta                                                19

<210> SEQ ID NO 54
<211> LENGTH: 19
<212> TYPE: DNA
<213> ORGANISM: Homo sapiens

<400> SEQUENCE: 54
gaaacaaacc ttacgtgaa                                                19

<210> SEQ ID NO 55
<211> LENGTH: 19
<212> TYPE: DNA
<213> ORGANISM: Homo sapiens

<400> SEQUENCE: 55
gattatggct acacgagct                                                19

<210> SEQ ID NO 56
<211> LENGTH: 19
<212> TYPE: DNA
<213> ORGANISM: Homo sapiens

<400> SEQUENCE: 56
gatggattct cttcgttca                                                19

<210> SEQ ID NO 57
<211> LENGTH: 19
<212> TYPE: DNA
<213> ORGANISM: Homo sapiens

<400> SEQUENCE: 57
tgtttcagct cttcgaact                                                19

<210> SEQ ID NO 58
<211> LENGTH: 19
<212> TYPE: DNA
<213> ORGANISM: Rattus sp.

<400> SEQUENCE: 58
cgactaatca gatgcgcaa                                                19

<210> SEQ ID NO 59
<211> LENGTH: 19
<212> TYPE: DNA
<213> ORGANISM: Rattus sp.

<400> SEQUENCE: 59
taaatgaaca gccgaaata                                                19

<210> SEQ ID NO 60
<211> LENGTH: 19
<212> TYPE: DNA
<213> ORGANISM: Rattus sp.

<400> SEQUENCE: 60
gcaggtagtt tgcgtgaaa                                                19

<210> SEQ ID NO 61
<211> LENGTH: 19
<212> TYPE: DNA
<213> ORGANISM: Artificial
<220> FEATURE:
```

```
<223> OTHER INFORMATION: Control siRNA sequence

<400> SEQUENCE: 61
gattttggcg acacaagct                                                    19
```

SUPPRESSION OF SCN9A GENE EXPRESSION AND/OR FUNCTION FOR THE TREATMENT OF PAIN

CROSS REFERENCE TO RELATED APPLICATIONS

This application is an application under section 371 of International Patent Application No. PCT/US2008/075409 filed Sep. 5, 2008 and which claims the benefit under 35 U.S.C. §119(e) to U.S. Provisional Patent Application No. 60/970,196 filed Sep. 5, 2007, the entire contents of which are incorporated herein by reference in their entirety.

FIELD OF THE INVENTION

The present invention relates to therapeutic down-regulation of SCN9A gene expression for the treatment of pain.

BACKGROUND OF THE INVENTION $Na_v1.7$ channels, voltage gated sodium channels, are encoded for by the gene SCN9A. These channels are preferentially expressed in peripheral sensory neurons of the dorsal root ganglia, which are involved in the perception of pain.

Mutations in the SCN9A gene have been associated with predispositions to pain hyper- or hypo-sensitivity. For instance, a role for the $Na_v1.7$ channel in pain perception was established by recent clinical gene-linkage analyses that revealed gain-of-function mutations in the SCN9A gene as the etiological basis of inherited pain syndromes such as primary erythermalgia (PE) and paroxysmal extreme pain disorder (PEPD). Alternatively, loss-of-function mutations of the SCN9A gene result in a complete inability of an otherwise healthy individual to sense any form of pain. Moreover, experimentally, a specific deletion of the SCN9A gene in transgenic mice drastically reduces their ability to perceive mechanical, thermal or inflammatory pain. This evidence suggests that increased levels of $Na_v1.7$ channels could enhance pain sensitivity whereas decreased levels of $Na_v1.7$ channels could reduce pain sensitivity.

The foregoing suggests that decreasing $Na_v1.7$ channel levels in peripheral sensory neurons of the dorsal root ganglia could provide an effective pain treatment. This approach could be beneficial due to several drawbacks associated with present pain treatments. For example, current pain therapies include drugs that are non-selective for their targets. This non-selectivity results in side effects involving the central nervous system (CNS). Therefore, more selective treatment options are needed.

One approach to provide local treatments is by reducing the expression and/or inhibiting the function of $Na_v1.7$ channel in the dorsal root ganglia. This reduction can be achieved in several ways, including through the genetic technology, RNA interference (RNAi) or other similar mechanisms. RNA interference allows the selective suppression of the expression of specific proteins, such as the $Na_v1.7$ channels. To understand the potential impact of this technology within the present invention, some background in the art is helpful.

Generally, for a protein, such as the $Na_v1.7$ channel, to exert a biological effect, the cell that will use the protein must create it. To create a protein the cell first makes a copy of the protein's gene sequence in the nucleus of the cell (in this instance, the sequence of the SCN9A gene that encodes for the $Na_v1.7$ channel protein). This copy of the gene sequence that encodes for the protein (called messenger RNA ("mRNA")) leaves the nucleus and is trafficked to a region of the cell containing ribosomes. Ribosomes read the sequence of the mRNA and create the protein for which it encodes. This process of new protein synthesis is known as translation. A variety of factors affect the rate and efficiency of protein translation. Among the most significant of these factors is the intrinsic stability of the mRNA itself. If the mRNA is degraded quickly within the cell (such as before it reaches a ribosome), it is unable to serve as a template for new protein translation, thus reducing the cell's ability to create the protein for which it encoded.

Based on the foregoing, the technology of RNAi has emerged. RNA interference is, in fact, a naturally-occurring mechanism for suppressing gene expression and subsequent protein translation. RNA interference reduces protein expression by either degrading the mRNA before it can be translated into a protein or by binding the mRNA and directly preventing its translation. This technology provides an avenue to suppress the expression of the SCN9A gene and resulting production of $Na_v1.7$ channels. A reduction in the number of $Na_v1.7$ channels in the peripheral sensory neurons of the dorsal root ganglia could decrease pain sensitivity.

SUMMARY OF THE INVENTION

The present disclosure provides RNA interference ("RNAi") and other similar pathways to suppress the expression of the SCN9A gene to reduce the amount of $Na_v1.7$ channels in the peripheral sensory neurons of the dorsal root ganglia. This reduction in $Na_v1.7$ channel levels could be used to treat pain associated with a variety of disorders. Importantly, the normal health of individuals containing a loss-of-function mutation of the $Na_v1.7$ channel is suggestive of a lack of any untoward effect of the therapies disclosed herein.

In one embodiment disclosed herein, method of treating pain is provided comprising administering to a mammal in pain a pharmaceutical composition comprising least one isolated nucleic acid molecule complementary to or identical to a target sequence of about 19 to about 25 contiguous nucleotides in SCN9A mRNA; and suppressing the expression and/or function of $Na_v1.7$ channels.

In an embodiment herein, provided is an isolated nucleic acid molecule comprising a sequence of about 19 to about 25 contiguous nucleotides that is complementary to a target sequence in SCN9A mRNA.

In one embodiment, the nucleic acid molecule is selected from the group consisting of siRNA, shRNA, antisense oligo (deoxy)nucleotides, ribozymes, aptamers, spiegelmers, and combinations thereof. In another embodiment, the nucleic acid molecule comprises one or more sequences are selected from the group consisting of SEQ ID NO 1; SEQ ID NO. 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10; SEQ ID NO 11; SEQ ID NO 12; SEQ ID NO 13; SEQ ID NO 14; SEQ ID NO 15; SEQ ID NO 16; SEQ ID NO 17; SEQ ID NO 18; SEQ ID NO 19; SEQ ID NO 20; SEQ ID NO 21; SEQ ID NO 22; SEQ ID NO 23; SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34; SEQ ID NO 35; SEQ ID NO 36; SEQ ID NO 37; SEQ ID NO 38; SEQ ID NO 39; SEQ ID NO 40; SEQ ID NO 41; SEQ ID NO 42; SEQ ID NO 43; SEQ ID NO 44; SEQ ID NO 45; SEQ ID NO 46; SEQ ID NO 47; SEQ ID NO 48; SEQ ID NO 49; SEQ ID NO 50; SEQ ID NO 51; SEQ ID NO 52; SEQ ID NO 53; SEQ ID NO 54; SEQ ID NO 55; SEQ ID NO 56; SEQ ID NO 57; SEQ ID NO 58; SEQ ID NO 59; and SEQ ID NO 60.

In another embodiment, the nucleic acid molecules are administered through a catheter and drug pump, via a controlled release polymer formulation or both.

In yet another embodiment, the nucleic acid molecule is in shRNA format and is delivered via a viral vector or a non-viral vector.

In another embodiment, the nucleic acid comprises a sense RNA strand and an antisense RNA strand, wherein the antisense RNA strand is complementary to the target sequence and the sense RNA strand is greater than 80% identical to the target sequence. In another embodiment, the sense and the antisense RNA strands are covalently linked by a single-stranded hairpin.

In another embodiment, the target sequence is a sequence unique to SCN9A.

In one embodiment, a pharmaceutical composition is provided comprising an effective amount of the isolated nucleic acid molecule complementary to or identical to a target sequence of about 19 to about 25 contiguous nucleotides in SCN9A mRNA; and suppressing the expression and/or function of $Na_v1.7$ channels.

In another embodiment, the use of an isolated nucleic acid molecule in the manufacture of a medicament for the treatment of pain is provided, the isolated nucleic acid molecule comprising a sequence of about 19 to about 25 contiguous nucleotides that is complementary to a target sequence in SCN9A mRNA.

BRIEF DESCRIPTION OF THE DRAWINGS

FIG. 3 depicts fluorescent imaging of the uptake of siRNA into dorsal root ganglions (DRG). FIG. 3A depicts DRG exposed to the siRNA transfection reagent alone and FIG. 3B depicts cells exposed to fluorescent siRNA with the transfection reagent. cb=cell body; dr=dorsal root.

DEFINITION OF TERMS

Figure 1A:
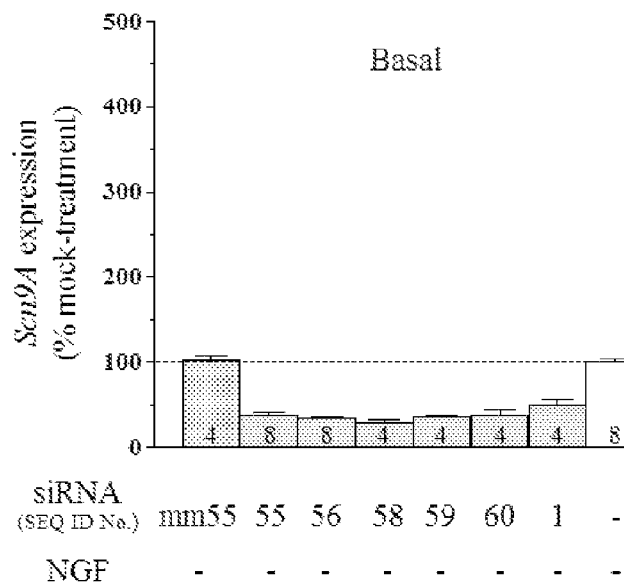
FIG. 1 depicts the effects of siRNA corresponding to SEQ ID NOs. 1, mm55, 55, 56 and 58-60 on SCN9A gene expression in rat pheochromocytoma cells in the absence (FIG. 1A) and presence (FIG. 1B) of nerve growth factor.

The term "SEQ ID NO: X" (where X is any number from 1 to 57) refers to, in one embodiment, each number's sequence as defined in the table included in (identified sequence). SEQ ID NO: X must also be read to encompass sequences that would hybridize under stringent conditions with the complementary strand of a sequence set forth in SEQ ID NOS: 1-57. Under this definition, claimed sequences can include at least 99% sequence homology with the identified sequence; at least 98% sequence homology with the identified sequence; at least 95% sequence homology with the identified sequence; at least 90% sequence homology with the identified sequence; or at least 85% sequence homology with the identified sequence.

The term "stringent conditions" as used herein refers to parameters with which those of ordinary skill in the art are familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York which are incorporated by reference herein for their disclosures regarding stringent hybridization conditions. In one embodiment stringent conditions can include hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 65° C. While this exemplary embodiment is provided, there are other conditions, reagents, and so forth that can used, that result in a similar degree of stringency. Those of ordinary skill in the art are familiar with such conditions, and thus they are not given here. It will be understood, however, that those of ordinary skill in the art will be able to manipulate the conditions in a manner to permit the clear identification of homologs and alleles of the nucleic acid sequences of the present invention. Those of ordinary skill in the art are also familiar with the methodology for screening cells and libraries for expression of such molecules which then are routinely isolated, followed by isolation of the pertinent nucleic acid molecule and sequencing.

The terms "nucleic acid" or "nucleic acid molecules" refer to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, described nucleic acid sequences also encompass conservatively modified variants thereof (e.g., degenerate codon substitutions) and complementary sequences, as well as the described sequence. Specifically, degenerate codon substitutions can be achieved by generating sequences in which the third position of one or more selected (or all) codons is substituted with mixed-base and/or deoxyinosine residues. The nucleic acid molecules of the present invention can include any type of nucleic acid molecule capable of mediating RNA interference, such as, without limitation, short interfering nucleic acid (siNA), short hairpin nucleic acid (shNA), short interfering RNA (siRNA), short hairpin RNA (shRNA), micro-RNA (miRNA), and double-stranded RNA (dsRNA). The nucleic acid molecules of the present invention also include similar DNA sequences and nucleic acid molecules including, without limitation, antisense oligo(deoxy)nucleotides, ribozymes, aptamers, and spiegelmers. Further, the nucleic acid and nucleic acid molecules of the present invention can contain unmodified or modified nucleotides. Modified nucleotides refer to nucleotides which contain a modification in the chemical structure of a nucleotide base, sugar and/or phosphate. Such modifications can be made to improve the stability and/or efficacy of nucleic acid molecules and are described in patents and publications such as U.S. Pat. Nos. 6,617,438; 5,334,711; 5,716, 824; 5,627,053; U.S. Patent Application No. 60/082,404, International Patent Cooperation Treaty Publication Number ("PCTPN") WO 98/13526; PCTPN WO 92/07065; PCTPN WO 03/070897; PCTPN WO 97/26270; PCTPN WO 93/15187; Beigelman et al., 1995, J. Biol. Chem., 270, 25702; Usman and Cedergren, 1992, TIBS. 17, 34; Usman et al., 1994, Nucleic Acids Symp. Ser. 31, 163; Burgin et al., 1996, Biochemistry, 35, 14090; Perrault et al. Nature, 1990, 344, 565-568; Pieken et al. Science, 1991, 253, 314-317; Usman and Cedergren, Trends in Biochem. Sci., 1992, 17, 334-339; Karpeisky et al., 1998, Tetrahedron Lett., 39, 1131; Earnshaw and Gait, 1998, Biopolymers (Nucleic Acid Sciences), 48, 39-55; Verma and Eckstein, 1998, Annu. Rev. Biochem., 67, 99-134; Burlina et al., 1997, Bioorg. Med. Chem., 5, 1999-2010; Limbach et al., 1994, Nucleic Acids Res. 22, 2183; and Burgin et al., 1996, Biochemistry, 35, 14090. Such patents and publications describe general methods and strategies to modify nucleic acid molecules and are incorporated by reference herein.

The phrase "expression cassette" as used herein means a nucleic acid sequence capable of directing expression of a particular nucleotide sequence in an appropriate host cell, with additional sequences that facilitate appropriate transcription of the nucleic acid sequence of interest. In addition to the nucleotide sequence of interest, the expression cassette can include a promoter operably linked to the nucleotide sequence of interest that also can be operably linked to termination and/or polyadenylation signals. The expression cassette also can include expression enhancers. The expression cassette including the nucleotide sequence of interest can be chimeric. The expression cassette also can be one that is naturally occurring but has been obtained in a recombinant form useful for heterologous expression. The expression of the nucleotide sequence in the expression cassette can be under the control of a constitutive promoter or of a regulatable promoter that initiates transcription only when the host cell is exposed to some particular stimulus. In the case of a multicellular organism, the promoter also can be specific to a particular tissue or organ or stage of development.

A "therapeutically effective amount" is the amount of drug sufficient to treat and/or ameliorate the pathological effects of pain, including but not limited to, hyperalgesia.

Pain as defined herein includes acute pain and chronic pain. "Chronic pain" includes inflammatory (nociceptive) and neuropathic pain associated with disorders including, but not limited to, cancer, arthritis, diabetes, traumatic injury and viral infections. Also included is pain due to inherited pain syndromes including, but not limited to primary erythermalgia (PE) and paroxysmal extreme pain disorder (PEPD).

The term "promoter" refers to a nucleotide sequence, usually upstream (5 prime) of the nucleotide sequence of interest, which directs and/or controls expression of the nucleotide sequence of interest by providing for recognition by RNA polymerase and other factors required for proper transcription. As used herein, the term "promoter" includes (but is not limited to) a minimal promoter that is a short DNA sequence comprised of a TATA-box and other sequences that serve to specify the site of transcription initiation, to which regulatory elements are added for control of expression. The term "promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. The term "enhancer" refers to a DNA sequence that can stimulate promoter activity and can be an innate element of the promoter or a heterologous element inserted to enhance the level or tissue specificity of a promoter. Enhancers are capable of operating in both orientations (normal or flipped), and are capable of functioning even when moved either upstream or downstream of the promoter. Both enhancers and other upstream promoter elements bind sequence-specific DNA-binding proteins that mediate their effects. Promoters can be derived in their entirety from a native gene, or be composed of different elements derived from different promoters found in nature, or even be comprised of synthetic DNA segments. A promoter also can contain DNA sequences that are involved in the binding of protein factors that control the effectiveness of transcription initiation in response to physiological or developmental conditions. Specific promoters used in accordance with the present invention can include, for example and without limitation pol II promoters (including, without limitation cytomegalovirus ("CMV") promoters, chicken β-actin ("CBA") promoters, Rous sarcoma virus ("RSV") promoters and neuron-specific enolase ("NSE") promoters). Furthermore, specific promoters used in accordance with the present invention can include, for example and without limitation, pol III promoters (including, without limitation, human H1 and human or murine U6 promoters, as well as H1 and U6 promoters engineered to be expressed in a regulated way such as described in United States Patent Application Number 2005/0064489).

The term "vector" is defined to include any virus, as well as any plasmid, cosmid, phage or binary vector in double or single stranded linear or circular form that may or may not be self transmissible or mobilizable, and that can transform eukaryotic host cells either by integration into the cellular genome or by existing extrachromosomally (e.g., autonomous replicating plasmid with an origin of replication).

DETAILED DESCRIPTION OF THE INVENTION $Na_v1.7$ channels, voltage gated sodium channels, are encoded for by the gene SCN9A. These channels are preferentially expressed in peripheral sensory neurons of the dorsal root ganglia, which are involved in the perception of pain.

Mutations in the SCN9A gene have been associated with predispositions to pain hyper- or hypo-sensitivity. For instance, recent clinical gene-linkage analyses revealed gain-of-function mutations in the SCN9A gene as the etiological basis of inherited pain syndromes such as primary erythermalgia (PE) and paroxysmal extreme pain disorder (PEPD). Moreover, loss-of-function mutations of the SCN9A gene result in a complete inability of an otherwise healthy individual to sense any form of pain. This evidence suggests that increased levels of $Na_v1.7$ channels could enhance pain sensitivity whereas decreased levels of $Na_v1.7$ channels could reduce pain sensitivity and that decreasing $Na_v1.7$ channel levels in peripheral sensory neurons of the dorsal root ganglia could provide an effective pain treatment.

One approach to provide local treatments is through the use of the genetic technology, RNA interference (RNAi). RNA interference allows the selective suppression of the expression of specific proteins, such as the $Na_v1.7$ channels. RNA interference is, in fact, a naturally-occurring mechanism for suppressing gene expression and subsequent protein translation. RNA interference reduces protein expression by either degrading mRNA before it can be translated into a protein or by binding the mRNA and directly preventing its translation. This technology provides an avenue to suppress the expression of the SCN9A gene and resulting production of $Na_v1.7$ channels. A reduction in the number of $Na_v1.7$ channels in the peripheral sensory neurons of the dorsal root ganglia could decrease pain sensitivity.

Reducing $Na_v1.7$ channel levels in the peripheral sensory neurons of the dorsal root ganglia could be used to treat pain associated with a variety of disorders including, without limitation, PE and PEPD as well as chronic and neuropathic pain. This approach could also be used to treat pain associated with, without limitation, arthritis, cancer, diabetes, traumatic injury, and viral infections. Importantly, the normal health of individuals containing a loss-of-function mutation of the Na$_v$1.7 channel is suggestive of a lack of any untoward effect of the therapy disclosed herein.

As stated, presented are methods and nucleic acid molecules for using RNAi to locally suppress expression of Na$_v$1.7 channels to treat pain. Specifically, RNAi is mediated by double stranded RNA ("dsRNA"), short hairpin RNA ("shRNA") or other nucleic acid molecules with similar characteristics. These nucleic acid molecules are processed or cut into smaller pieces by cellular enzymes including Dicer and Drosha. The smaller fragments of the nucleic acid molecules can then be taken up by a protein complex (the RISC complex) that mediates degradation of mRNAs. The RISC complex will degrade mRNA that complementarily base pairs with the nucleic acid molecules it has taken up. In this manner, the mRNA is specifically destroyed, thus preventing the encoded-for protein, Na$_v$1.7 channels, from being made. Other similar intracellular mechanisms may similarly be used to suppress the expression of the SCN9A gene.

The described understanding of the mechanism of RNAi and similar pathways now allows the creation of nucleic acid molecules with sequences that are homologous to known gene sequences in order to suppress the expression or formation of certain proteins within a cell. In this present disclosure, nucleic acid molecules that complimentarily bind to Na$_v$1.7 channel mRNA sequences can be introduced into cells locally to suppress expression of these proteins. Suppressing expression of this protein can locally treat pain in an area without requiring a less specific treatment that more globally affects the central nervous system.

The following nucleotide sequences were identified to selectively suppress the expression of the SCN9A gene and resulting Na$_v$1.7 channels and target the rat (NM_133289) or human (NM_002977) SCN9A sequence. Note that, as will be understood by one of ordinary skill in the art, the nucleic acid molecules of the present invention include the sequences in Table 1, the reverse complement of these sequences and RNA-based sequences including uracils in the place of the listed thymidines. Thus, the sequences in Table 1 may be considered target sequences as well as sequences included in the nucleic acid molecules of the present invention.

TABLE 1

| SEQ ID NO: | Target Gene* | Nucleotide Base Sequence | Start Position in SCN9A Gene |
|---|---|---|---|
| 1 | rScn9a | GGGAATCAATTACGTGAAA | 2988 |
| 2 | rScn9a | CATTAAATCTCTACGGACA | 3849 |
| 3 | rScn9a | AGGAAGAAGCTGAGGCGAT | 1301 |
| 4 | rScn9a | GAGGAAAGCATCCGAAAGA | 1513 |
| 5 | hScn9a | CAGAAGAACAGAAGAAATA | 4439 |
| 6 | hScn9a | TGAAGAAGCTAAACAGAAA | 1287 |
| 7 | hScn9a | GGTAAGAGCTACAAAGAAT | 2680 |
| 8 | hScn9a | AGGCAGAGGAAGAGATATA | 1722 |
| 9 | hScn9a | AGACAGAGATGATGATTTA | 5775 |
| 10 | hScn9a | GGGAAAGACAGCAAGGAAA | 5953 |
| 11 | hScn9a | GAACAAGACAGAACAGAAA | 5923 |
| 12 | hScn9a | GTGAAGAAGACTTTAGAAA | 932 |
| 13 | hScn9a | CCAAAGATTTCCAGGGAGA | 3067 |
| 14 | hScn9a | TAACATAGAGTCAGGGAAA | 3519 |
| 15 | hScn9a | GAAAGAAGAAACAGAAGAA | 1471 |
| 16 | hScn9a | GGAGATAAGACAAGCAGAA | 3081 |
| 17 | hScn9a | CTGAATACTAAGAAGGAAA | 3103 |
| 18 | hScn9a | GAGAAGAAGCAGAGGCTGA | 3428 |
| 19 | hScn9a | GAAAGATGATGATGAAGAA | 165 |
| 20 | hScn9a | TGGGAAACCTGAAGCATAA | 851 |
| 21 | hScn9a | GAACACAGTTGGTTTGAAA | 3583 |
| 22 | hScn9a | TGACAGAAGAACAGAAGAA | 4436 |
| 23 | hScn9a | AAGAAGAAGCTGAGGCAAT | 1349 |
| 24 | hScn9a | TTTCAAAGGCAGAGGAAGA | 1716 |
| 25 | hScn9a | CTTGAAGAGTCCAGACAAA | 2122 |
| 26 | hScn9a | GCTAAAGAAAGAAGAAACA | 1465 |
| 27 | hScn9a | AGAAGAAACAGAAGAAAGA | 1474 |
| 28 | hScn9a | GCTGAGAAATTGTCGAAAT | 1537 |
| 29 | hScn9a | GAGCAAGCATATTAACAAA | 2090 |
| 30 | hScn9a | CATAAAAGATGGAGACAGA | 5763 |
| 31 | hScn9a | TAACAAAGCCAGACAAAGA | 5897 |
| 32 | hScn9a | AAAGGAAGACAAAGGGAAA | 5940 |
| 33 | hScn9a | AAAGGGAGATGCTGAGAAA | 1527 |
| 34 | hScn9a | TAACAAACACTGTGGAAGA | 2102 |
| 35 | hScn9a | AGTATTGAACAAAGGGAAA | 315 |
| 36 | hScn9a | AGGCGAAGCAGCAGAACAA | 1687 |
| 37 | hScn9a | TAGCAGATGTGGAAGGATT | 2489 |
| 38 | hScn9a | AAACAAACCTTACGTGAAT | 3022 |
| 39 | hScn9a | AAATATGAATGCTGAGGAA | 3312 |
| 40 | hScn9a | CCAAAGAAGAAAAGAAAGA | 152 |
| 41 | hScn9a | CTGACAAACTGCATATTTA | 457 |
| 42 | hScn9a | AGGGAGATGCTGAGAAATT | 1529 |
| 43 | hScn9a | CATTGAACATGCTGATTAA | 2567 |
| 44 | hScn9a | GCATGCAGCTCTTTGGTAA | 2666 |
| 45 | hScn9a | AGACAATCTTACAGCAATT | 2934 |
| 46 | hScn9a | AAGAAGACCCTGATGCAAA | 2954 |
| 47 | hScn9a | GGAAGACAGTGATGGTCAA | 3228 |
| 48 | hScn9a | CAGACAAGATCTTCACTTA | 3701 |
| 49 | hScn9a | AGCCAGACAAAGAGAAATA | 5903 |
| 50 | hScn9a | CTTCGAACTTTCAGAGTAT | 685 |

TABLE 1-continued

| SEQ ID NO: | Target Gene* | Nucleotide Base Sequence | Start Position in SCN9A Gene |
|---|---|---|---|
| 51 | hScn9a | GAGTAGAGCAAGCATATTA | 2085 |
| 52 | hScn9a | TGTACTTGCTATAGGAAAT | 2337 |
| 53 | hScn9a | GGTCAAGCTATGTGCCTTA | 2833 |
| 54 | hScn9a | GAAACAAACCTTACGTGAA | 3021 |
| 55 | rScn9a and hScn9a | GATTATGGCTACACGAGCT | 1012 |
| 56 | rScn9a and hScn9a | GATGGATTCTCTTCGTTCA | 5559 |
| 57 | rScn9a and hScn9a | TGTTTCAGCTCTTCGAACT | 627 |
| 58 | rSCN9A | CGACTAATCAGATGCGCAA | 1976 |
| 59 | rSCN9A | TAAATGAACAGCCGAAATA | 4256 |
| 60 | rSCN9A | GCAGGTAGTTTGCGTGAAA | 8686 |
| 61 (mm55) | Control siRNA | GATTTTGGCGACACAAGCT | N/A |

*r = rat; h = human

To identify which nucleic acid sequence most effectively suppresses $Na_v1.7$ channel expression, an in vitro transfection assay system is used, wherein the nucleic acid molecule is transfected into cells endogenously expressing the SCN9A gene. Examples of cells endogenously expressing the SCN9A gene include, but are not limited to, primary cultures of the dorsal root ganglia and neuroblastoma cells (e.g. IMR-32). Alternatively, $Na_v1.7$ channel (SCN9A) gene sequences can be subcloned into pTracer™-CMV2 (Invitrogen, Corp., Carlsbad, Calif.) to generate pTracer-$Na_v1.7$ channels. This recombinant plasmid also includes a GFP-Zeocin reporter gene for transfection efficiency normalization. The CMV promoter directs constitutive expression of the target gene (SCN9A) while the EF1 promoter directs constitutive expression of the GFP-Zeocin reporter gene. The generated recombinant plasmids are used to facilitate screening of nucleic acid sequences by co-transfection into a eukaryotic cell line. Specifically, HEK293 or HeLa cell cultures at 60-70% confluency are co-transfected with the appropriate target plasmid (2 μg/well of a 6-well plate) and test nucleic acid sequences directed against SCN9A. Forty-eight hr post-transfection of the cells endogenously expressing SCN9A or cells co-transfected with the recombinant target/reporter plasmid, total cellular RNA is harvested from the cells and used to make cDNA by standard methods. The cDNAs are analyzed for target (SCN9A) and housekeeping gene (e.g. GAPDH or 18S rRNA) or SCN9A and reporter (GFP) gene expression levels using realtime (RT)-PCR methods, respectively. The data can be normalized for housekeeping gene or GFP expression levels as appropriate.

The siNA (small interfering nucleic acid) sequences and molecules of the present disclosure can be manipulated to enhance their uptake into the RISC complex. Specifically, manipulating the 3 prime terminal nucleotide of the sense strand can be highly advantageous. Preferential entry of the guide, or antisense, strand into RISC can be achieved by introducing 3 prime mismatches in the sense strand while maintaining perfect base pairing (of the antisense strand and the intended mRNA target) at the 5 prime terminus of the antisense strand. This maximizes entry of the antisense strand into the RISC complex, while also reducing potential off-target inhibition by the sense strand. Therefore, the sense and antisense strands of nucleic acid compositions are not required to be identical. In one embodiment, the antisense RNA strand is complementary to the target sequence and the sense RNA strand is greater than 80% identical to the target sequence. In additional embodiments the identity is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical.

In another embodiment, the sense strand is greater than 80% complementary to the antisense strand. In additional embodiments the complementarity is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% complementary.

Aptamers are single or double stranded D-nucleic acids that specifically interact with and bind to a target molecule, thus interfering with its function. The manufacture or selection of aptamers is described in, for example, European patent EP 0 533 838 which is incorporated by reference herein. Briefly, a mixture of nucleic acids is provided whereby each nucleic acid typically comprises a segment of several (in certain embodiments at least eight) randomized nucleotides. The mixture is contacted with the target molecule whereby those nucleic acids with a higher affinity to the target molecule bind the target molecule to a greater extent than the rest of the candidate mixture. The binding nucleic acid(s) are then separated from the remainder of the mixture and can be amplified using standard PCR techniques.

Spiegelmers are similar to aptamers but are composed of L-nucleotides rather than D-nucleotides. The manufacture of spiegelmers is described in, for example, international patent application WO 98/08856 which is incorporated by reference herein. Briefly, in the process of generating spiegelmers, a heterogenous population of D-nucleic acids is created and contacted with the optical antipode of the target molecule. Subsequently, the D-nucleic acids that interact with the optical antipode of the target molecule are separated and sequenced. The L-nucleic acids that correspond to the sequenced D-nucleic acids are then synthesized. These L-nucleic acids will specifically interact with the naturally occurring target molecule rather than with the optical antipode thereof, thus impairing the target molecule's function.

The design and use of ribozymes are also known to those of ordinary skill in the art, and are described in, for example, Doherty and Doudna, 2001, Annu Ref. Biophys. Biomolstruct. 30, 457-75 and Lewin and Hanswirth, 2001, Ribozyme Gene Therapy: Applications for Molecular Medicine, 7: 221-8 which are incorporated by reference herein. Ribozymes are catalytically active nucleic acids which preferably consist of two RNA moieties. The first moiety shows catalytic activity whereas the second is responsible for the ribozyme's specific interaction with the target nucleic acid, in the present case the nucleic acid coding for $Na_v$ 1.7 channels. Upon interaction between the target nucleic acid and the second moiety of the ribozyme (typically by hybridization and Watson-Crick base pairing), the catalytically active moiety catalyses the target nucleic acid.

Antisense oligo(deoxy)nucleotides function based on a similar mode of action. Basically, antisense oligo(deoxy) nucleotides hybridize with a target RNA due to base complementarity. Binding of the target RNA by the antisense oligo (deoxy)nucleotide activates RNase H which degrades the RNA. Antisense oligo(deoxy)nucleotides are described in, for example, U.S. Pat. Nos. 5,849,902 and 5,989,912 which are incorporated by reference herein.

Methods of producing siRNA, 21-23 nucleotides (nt) in length from an in vitro system and use of the siRNA to interfere with mRNA of a gene in a cell or organism were described in WO0175164 A2, the contents of which is entirely incorporated herein by reference.

The siRNA can also be made in vivo from a mammalian cell using a stable expression system. For example, a vector system, named pSUPER, that directs the synthesis of small interfering RNAs (siRNAs) in mammalian cells, was recently reported (Brummelkamp et al., (2002) Science 296: 550-3), and the contents of which is incorporated herein by reference. On the pSUPER, the H1-RNA promoter was cloned in front of the gene specific targeting sequence (19-nt sequences from the target transcript separated by a short spacer from the reverse complement of the same sequence) and five thymidines (T5) as a termination signal. The resulting transcript is predicted to fold back on itself to form a 19-base pair stem-loop structure, resembling that of *C. elegans* Let-7. The size of the loop (the short spacer) is preferably 9 bp. A small RNA transcript lacking a poly-adenosine tail, with a well-defined start of transcription and a termination signal consisting of five thymidines in a row (T5) was produced. Most importantly, the cleavage of the transcript at the termination site is after the second uridine yielding a transcript resembling the ends of synthetic siRNAs, that also contain two 3' overhanging T or U nucleotides. The siRNA expressed from pSUPER is able to knock down gene expression as efficiently as the synthetic siRNA.

The present disclosure provides a method of treating pain in a subject in need thereof, comprising the steps of (a) introducing siRNA that targets the mRNA of the SCN9A gene for degradation into the cell or organism; (b) maintaining the cell or organism produced (a) under conditions under which siRNA interference of the mRNA of the SCN9A gene in the cell or organism occurs. The siRNA can be produced chemically via nucleotide synthesis, from an in vitro system similar to that described in WO0175164, or from an in vivo stable expression vector similar to pSUPER described herein. The siRNA can be administered similarly as that of anti-sense nucleic acids.

Physical methods to introduce nucleic acid molecules and/or their carriers (i.e. vectors) into eukaryotic cells are known in the art. Some of these methods include, without limitation, calcium phosphate or calcium chloride co-precipitation, DEAE-dextran-mediated transfection, cationic lipid-mediated transfection, lipofection, protoplast fusion, particle bombardment, microinjection, liposome fusion, biolistics and other suitable methods found in, for example, Sambrook, et al. (Molecular Cloning: A Laboratory Manual, 2nd, ed, Cold Spring Harbor Laboratory, Cold Spring Harbor Laboratory Press, Cold Spring Harbor, N.Y., 1989), and other laboratory manuals. Further, biological methods to introduce nucleic acid molecules into a cell include the use of viral vectors. For mammalian gene therapy, viral vectors, and especially retroviral vectors, have become the most widely used method for inserting genes into mammalian cells. Other viral vectors can be derived from poxviruses, herpes simplex virus I, adenoviruses and adeno-associated viruses, and the like (see, for example, Boenisch et al., U.S. Pat. No. 5,350,674 and Wilson et al., U.S. Pat. No. 5,585,362 which are hereby incorporated by reference). Non-viral vectors may also be used.

The nucleic acid molecules/vehicle combinations of the present disclosure can be delivered as intermittent injections of siRNA with a transfection reagent such as, without limitation, siStable, PEI, or iFect, or pump-mediated infusions of siRNA into the intrathecal space. Other methods include locally delivered by catheter and drug pump systems, delivered by direct local injection or through the use of polymers and/or drug-eluting stents as described in co-pending U.S. patent application Ser. No. 10/972,157 which is incorporated herein by reference. In one embodiment, a "controlled administration system" including a direct and local administration system can be used. A controlled administration system can be a depot or a pump system, such as, without limitation, an osmotic pump or an infusion pump. An infusion pump can be implantable and can be, without limitation, a programmable pump, a fixed rate pump, and the like. A catheter can be operably connected to the pump and configured to deliver agents of the present invention to a target tissue region of a subject. A controlled administration system can be a pharmaceutical depot (a pharmaceutical delivery composition) such as, without limitation, a capsule, a microsphere, a particle, a gel, a coating, a matrix, a wafer, a pill, and the like. A depot can comprise a biopolymer. The biopolymer can be a sustained-release biopolymer. The depot can be deposited at or near, generally in close proximity, to a target site. Embodiments of the present compositions also can be delivered through the use of liposomes, polyethyleneimine, by iontophoresis, or by incorporation into other vehicles, such as biodegradable nanocapsules.

The nucleic acid molecules/vehicle combinations can be locally delivered by catheter and drug pump systems, delivered by direct local injection or through the use of polymers and/or drug-eluting stents as described in co-pending U.S. patent application Ser. No. 10/972,157 which is incorporated by reference herein. In one embodiment, a "controlled administration system" including a direct and local administration system can be used. A controlled administration system can be a depot or a pump system, such as, without limitation, an osmotic pump or an infusion pump. An infusion pump can be implantable and can be, without limitation, a programmable pump, a fixed rate pump, and the like. A catheter can be operably connected to the pump and configured to deliver agents of the present invention to a target tissue region of a subject. A controlled administration system can be a pharmaceutical depot (a pharmaceutical delivery composition) such as, without limitation, a capsule, a microsphere, a particle, a gel, a coating, a matrix, a wafer, a pill, and the like. A depot can comprise a biopolymer. The biopolymer can be a sustained-release biopolymer. The depot can be deposited at or near, generally in close proximity, to a target site. Embodiments of the instant nucleic acids can also be delivered through the use of liposomes, polyethyleneimine, by iontophoresis, or by incorporation into other vehicles, such as biodegradable nanocapsules.

In certain embodiments, the delivery of RNAi or other nucleic acid molecule tools can incorporate the use of Medtronic products, ranging from pumps (e.g. Medtronic's Synchromed pump) to deliver short interfering RNA into the intrathecal space of the spinal cord to devices (e.g. Medtronic's Stealth Station, Navigus, and catheters) for delivering a viral or non-viral construct that encodes a short hairpin RNA in the neurons of the dorsal root ganglion.

With the predominant expression of SCN9A in the dorsal root ganglion (DRG; see Raymond et al., 2004, J. Biol. Chem., 279, 46234-46241) and a critical role for DRGs in processing pain signals, an important feature of the delivery agent must be to enable the introduction of the therapeutic molecule (e.g. siRNA) into the cell bodies of DRGs.

In assessing the methods of introducing siRNA, administration effectiveness can be evaluated in treated rodents using behavioral model(s) of mechanical, thermal, and inflammatory pain, for example, as demonstrated for the SCN9A-knockout mice by Nassar et al. 2004, PNAS, 101, 12706-12711 (and the references within) which are all incorporated by reference herein. For instance, molecule effectiveness can be evaluated using the formalin or CFA pain models or by using a tactile allodynia test. These methods are well known to those of ordinary skill in the art and thus are not described further herein. For reference, however, the reader is directed to Kim and Chung, 1992, Pain 50:355-363; Yaksh and Rudy, 1976, Physiol Behav 17:1031-1036; Tsuda et al., 2004, Glia, 89:89-95; Dixon, 1980, Ann Rev Pharmacol Toxicol 20:441-462 and Chaplan et al., 1994, J Neurosci Methods 53:55-63 all of which are incorporated by reference herein.

Finally, another application of the presently disclosed methods and compositions includes a potential therapy for prostate cancer as the $Na_v1.7$ channel bears metastatic potential, and upregulated levels have been detected in biopsies of human prostate cancer. Therefore, the presently described sequences and methods could have important implications beyond the treatment of pain.

As should be understood, the exact formulation, route of administration, and dosage should generally be determined by the attending physician in view of the patient's condition. Dosage amount and interval can be adjusted individually to provide appropriate levels of nucleic acid molecules which are sufficient to maintain therapeutic effect.

It is to be understood that the presently disclosed compositions and methods are not limited to the particular embodiments, materials, and examples described herein, as these can vary. For example, the nucleic acid molecules of the present invention can be created in a variety of formats and lengths. Indeed, those skilled in the art will recognize that the most important attribute of the nucleic acid molecules of the present invention is their ability to complementarily bind to the mRNA sequences of interest to reduce the mRNA stability and/or the translation rate of these sequences. The phrase "complementarily bind" as used herein, refers to the abilities of the nucleic acid molecules to form hydrogen bond(s) with mRNA sequences by either traditional Watson-Crick pairing or other non-traditional types. While binding due to 100% complementarity is preferred, complementarity as low as 50-75% also is useful in accordance with the methods of the disclosed herein.

As stated, the nucleic acid molecules can include any type of nucleic acid molecule capable of mediating RNA interference, such as, without limitation, short interfering nucleic acid (siNA), short hairpin nucleic acid (shNA), short interfering RNA (siRNA), short hairpin RNA (shRNA), micro-RNA (miRNA), and double-stranded RNA (dsRNA). The nucleic acid molecules of the present invention also include similar DNA sequences and nucleic acid molecules that can suppress SCN9A channel expression outside of the RNAi cellular pathway including, without limitation, antisense oligo(deoxy)nucleotides, ribozymes, aptamers, and spiegelmers. Further, these nucleic acid molecules can contain unmodified or modified nucleotides as previously described.

Again, as stated, the nucleic acid molecules can be created in a variety of lengths. Any length can be used so long as the nucleic acid molecules of the present invention complementarily bind to the mRNA sequences of interest to reduce the mRNA stability and/or the translation rate of these sequences.

In one embodiment of the methods and nucleic acid molecules, the molecules are about 19-21 base pairs. In another embodiment, the molecules are about 25-27 base pairs. Again, however, these lengths are non-limiting examples.

As disclosed herein, pharmaceutical compositions are provided that inhibit the expression of the SCN9A gene or reduce the levels of $Na_v1.7$ voltage gated sodium channels at the protein level. Once one or more target sites have been identified, oligonucleotides are chosen which are sufficiently complementary to the target, i.e., hybridize sufficiently well and with sufficient specificity, to give the desired effect, using, for example, any of the techniques mentioned herein.

RNA aptamers can also be introduced into or expressed in a cell to modify RNA abundance or activity. RNA aptamers are specific RNA ligands for proteins, such as for Tat and Rev RNA (Good et al., 1997, Gene Therapy 4: 45-54) that can specifically inhibit their translation.

Double-stranded RNA (dsRNA) can also be used to inhibit gene expression by a mechanism generally known in the art as RNA interference (RNAi). RNAi is described for instance in U.S. Pat. No. 6,506,559 or in Patent Applications WO0244321 or WO0175164, the contents of which are herewith incorporated by reference. The length of the dsRNA is not crucial for RNAi according to the presently disclosed methods, however, preferred dsRNAs are such which are generally known in the art as small-inhibitory RNAs (siRNAs). In a preferred embodiment, the siRNAs are short dsRNAs having a length of 19 to 25 nucleotides. Most preferred are dsRNAs having a length of 21 to 23 nucleotides. The dsRNAs may be blunt ended or ligated at or on at least one end with either loops composed of ribonucleotides or deoxyribonucleotides or a chemical synthetic linker (WO00/44895). In a one embodiment, the ribonucleic acid contains 3'-end nucleotide overhangs on the antisense strand and/or the sense strands of the dsRNA of at least one ribonucleotide or deoxyribonucleotide, or modified nucleotide. Also suitable are overhangs with 1, 2, 3 or 4 nucleotides. The overhangs may contain both ribonucleotide(s) and deoxyribonucleotide(s) which in addition may contain modified sugar moieties. The overhang may be of any sequence, but in a one embodiment, the overhang is complementary to the target mRNA strand. In another embodiment the overhang contains at least one UU group or dTdT group. In another embodiment, the overhang on the antisense strand has the penultimate overhanging nucleotide complementary to the mRNA target strand. In one example, such an overhang is a 2-nucleotides overhang. In a further embodiment, the overhang is composed of 4 Us. In another embodiment, the extreme 3'-position of the siRNA is a hydroxyl group. Additionally, the 5'-end may be a hydroxyl or phosphate group.

In related aspect, the present disclosure provides the use of one or more antisense or siRNA molecules that specifically inhibit the expression of the SCN9A gene for the manufacture of a medicament useful in the treatment of pain.

Gene specific inhibition of gene expression may also be achieved using conventional double stranded RNA technologies. A description of such technology may be found in WO 99/32619 as well as Harborth J; et al., Journal of Cell Science (2001 December), 114(Pt 24), 4557-65, and the entire contents of both references are hereby incorporated by reference.

Antisense molecules, RNA aptamers, and double-stranded RNA may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding the genes of the polypeptides discussed herein. Such DNA sequences may be incorporated into a wide variety of vectors with suitable RNA polymerase promoters such as T7 or SP6. Alternatively, cDNA constructs that synthesize antisense RNA constitutively or inducibly can be introduced into cell lines, cells, or tissues.

The compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition to the formulations described previously, the compositions may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions suitable for use in the invention include compositions wherein the active ingredients are contained in an effective amount to achieve the intended purpose.

A therapeutically effective dose refers to that amount of active ingredient, for example, antisense oligonucleotides, RNA aptamer or double stranded RNA designed to inhibit SCN9A gene expression, useful to treat and/or ameliorate the pathological effects of pain. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The data obtained from cell culture assays and animal studies are used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Advantageously, compositions presented herein may be administered in a single daily dose, or the total daily dosage can be administered in divided doses of two, three or four times daily. Furthermore, the compositions can be administered topically or via transdermal routes, using, for example, transdermal patches, as are well known to those of ordinary skill in that art. Preferably, the compositions may be administered over an extended time period to produce analgesic therapy by a transdermal controlled release-rate mechanism as described in U.S. Pat. No. 5,914,131. Dosage may also be administered intravenously, by intramuscular injection, or by injection in the vicinity of a nerve, ganglion or the spinal cord.

Furthermore, the compositions can be administered intrathecally by bolus injection or by implantation of a pump to provide continuous administration of the composition over a pre-determined, beneficial period of time.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

EXAMPLE 1

Down-regulation of SCN9A in Rat Pheochromocytoma Cells

Figure 1B:
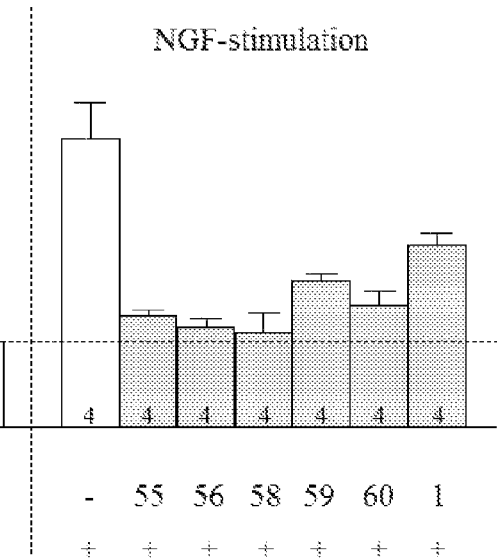

In the example demonstrated in FIG. 1, siRNAs were screened for their ability to down-regulate the expression of SCN9A in rat pheochromocytoma (PC12) cells. PC12 cells were transfected with siRNAs, as denoted by their SEQ ID numbers in the table above. The siRNA identified as SEQ ID NO: mm55 comprises the siRNA of SEQ ID NO: 55 incorporating 3 mismatches in the sequence at positions 5, 10, and 15 of the antisense strand. The siRNAs SEQ ID NO: 58, SEQ ID NO: 59 and SEQ ID NO: 60 comprise siRNA sequences recommended by Dharmacon (Lafayette, Colo.) for targeting the rat SCN9A mRNA sequence. Cells were transfected with siRNA (100 nM) using Lipofectamine 2000 transfection reagent (per the manufacturer's protocol, Invitrogen; Carlsbad, Calif.), and were cultured for 48 hours. In some cases, cells were stimulated with nerve growth factor (NGF, 10 ng/ml final concentrations) for the last 5 hours of the 48 hour siRNA-incubation period. NGF-mediated stimulation of SCN9A expression has been well characterized in PC12 cells (D'Arcangelo et al., J. Cell Biology, 122:915-921, 1993). Total cell RNA was harvested at the end of the 48 hour period, and cDNA was made using standard methods. The cDNAs were analyzed for target (SCN9A) and housekeeping gene (GAPDH) mRNA expression levels using RT-PCR. The data were normalized for GAPDH expression levels. All siRNAs tested, including the rat (NM_133289) as well as human (NM_002977) SCN9A-targeting siRNAs (Sequence ID nos. 55 and 56) demonstrated a significant down-regulation of SCN9A expression levels relative to the expression levels in mock- or mismatch siRNA-treated cells (P<0.01; using one-way ANOVA followed by Tukey's or Dunnett's post-hoc test as appropriate). SiRNA-mediated down-regulation was evident for both endogenous and NGF-stimulated SCN9A expression levels in PC12 cells. The number of experiments is indicated within individual bars representing each group.

EXAMPLE 2

Requirement for Entry of siRNA into DRG Cell Bodies

Figure 2A:
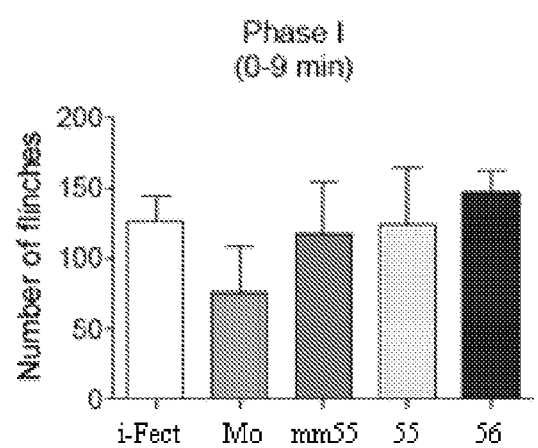
FIG. 2 depicts the effects of siRNA corresponding to SEQ ID NOs. mm55, 55 and 56 on flinching in both Phase I (0-9 min after formalin administration, FIG. 2A) and Phase II (10-60 min after formalin administration, FIG. 2B) in a formalin-induced inflammatory pain model in rats.
Figure 2B:
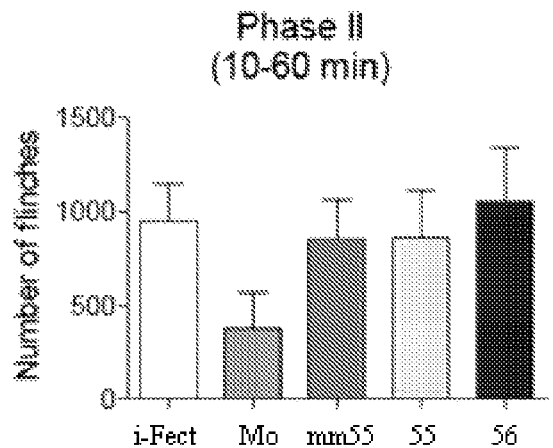

In the example below, data is presented regarding the requirement of introducing the siRNA into the cell bodies of the DRG. Male Sprague Dawley rats (Harlan, Indianapolis, Ind.) with a weight range of 225-245 grams were catheterized (on day 0) for epidural administration of siRNA. On days 4 through 7, 7 μg of siRNA with sequence ID nos. 55, 56, or mm55 (identified above) were complexed with a cationic lipid transfection reagent, i-Fect™, as described by the supplier (Neuromics, Edina, Minn.), and injected once daily through the epidural catheter. Vehicle (equivalent amount of i-Fect™ alone in the siRNA re-suspension buffer from Qiagen, Valencia, Calif.) or the siRNA re-suspension buffer alone were epidurally injected as controls. Five rats were dedicated per treatment group. Catheter patency was verified throughout the experiment using standard procedures. On day 8, the formalin test was performed to evaluate the rat's response to inflammatory pain. Fifteen minutes prior to formalin injection in the paw, morphine sulfate (50 μg) was injected via the epidural catheter in the siRNA re-suspension buffer-injected group. This group served as a positive control for detecting a decrease in the rat's behavioral response (number of flinches) to formalin-induced inflammatory pain (shown in FIG. 2), particularly in the 10- to 60-minute time interval (phase II) after formalin injection. The rats treated with siRNAs demonstrated a behavior response equivalent to that exhibited by rats that were treated with the vehicle control. At the end of behavior testing, rats were sacrificed and L4 through L6 DRGs were harvested for analysis of SCN9A expression as described earlier. Correlating with an inability to reduce formalin-induced pain, SCN9A expression was unaltered in the DRGs from rats treated with any of the siRNA groups. The experiment was repeated with fluorophore-labeled stabilized siRNA (siGLO RISC-Free siRNA; Dharmacon) complexed with i-Fect™ to determine the localization of siRNAs relative to the cell bodies of DRGs. Rats were transcardially perfused with saline and then paraformaldehyde (4% in saline) at the end of the experiment. Lumbar DRGs were harvested, embedded in paraffin, and sectioned to visualize the red fluorescence emitting from siGLO siRNA during fluorescence microscope imaging. Cell nuclei were stained with DAPI to fluoresce blue during imaging. Tissues were imaged for red and blue fluorescence and images were merged to reveal that all of the red fluorescence was restricted to the dorsal root (dr), and there was a lack of fluorophore-labeled siRNA in the cell bodies of lumbar DRGs (representatives shown in FIG. 3) with the method employed to deliver siRNAs. This example highlights the significance of introducing SCN9A-targeting siRNAs in the cell bodies of DRGs in order to achieve a reduction in SCN9A expression in the DRGs and a beneficial analgesic response to painful stimuli.

EXAMPLE 3

Effect of SCN9A siRNA on Rats in the Seltzer Model of Chronic Pain

In order to evaluate the effect of siRNAs in vivo, for example, rats (e.g. Wistar) may be intrathecally cannulated in the lumbar or thoracic region of the spinal cord with a catheter attached to a minipump delivery system according to conventional methods. siRNAs or vehicle may then be delivered for up to 7 days at a desired concentration to allow cell bodies within the spinal cord and the dorsal root ganglia to take up the siRNAs or vehicle. Nerve injury may be performed either before or after cannulation according to the pain models described herein. Mechanical hyperalgesia, allodynia, etc may be measured according to conventional methods to assess the effect of SCN9A siRNAs in reversal of hyperalgesia.

In this case, the partial sciatic ligation (Seltzer) model of neuropathic pain is used as previously described (Seltzer Z, Dubner R, Shir Y, 1990, Pain 43:205-218). Briefly, male Wistar rats (120-140 g) are anesthetized, the left sciatic nerve exposed at mid-thigh level through a small incision and ⅓ to ½ of the nerve thickness tightly ligated with a 7.0 silk suture. The wound is closed with sutures and clips and the wound dusted with antibiotic powder. In sham animals the sciatic nerve is exposed but not ligated and the wound closed as before. Mechanical hyperalgesia is assessed by measuring paw withdrawal thresholds of both hindpaws to an increasing pressure stimulus using an Analgesymeter (Ugo-Basile, Milan). The cut-off is set at 250 g and the end-point taken as paw withdrawal, vocalisation or overt struggling. The statistical significance of mechanical hyperalgesia data obtained from the different experimental animal groups is analyzed using ANOVA followed by Tukey's HSD test.

siRNAs are administered to rats intrathecally via an indwelling cannula, inserted 24 h prior to or 14 days following sciatic nerve ligation, (or 24 h prior to injection of Complete Freund's Adjuvant or formalin into a hindpaw if one uses an inflammatory pain model). Rats are anesthetised and an incision made in the dorsal skin just lateral to the midline and approximately 10 mm caudal to the ventral iliac spines. A sterile catheter (polyethylene PE10 tubing) is inserted via a guide cannula (20 gauge needle) and advanced 3 cm cranially in the intrathecal space approximately to the L1 level. The catheter is then connected to an Alzet mini osmotic-pump (Alza Corporation, Palo Alto, Calif.) delivering siRNA or vehicle which is inserted subcutaneously in the left or right flank. The incision is closed with wound clips and dusted with antibiotic powder.

Results indicate that the intrathecal administration of SCN9A siRNA over 7 days on established neuropathic mechanical hyperalgesia in rats results in an increase in withdrawal threshold in the paw pressure test, representative of decreased mechanical hyperalgesia. This effect is not seen following similar administration of saline (vehicle).

EXAMPLE 4

Effects of SCN9A siRNA on Mechanical Allodynia in Rats with Neuropathic Pain

Four groups of rats are ligated on the left hind limb on day 0 and base line mechanical allodynia is measured. An additional unligated group (naive) is set up as control. Rats are cannulated on day 10 and infused with vehicle, siRNA or control for a further 6 days. Von Frey thresholds on the left paw are measured daily. Vehicle: isotonic buffer, n=8/treatment group. The right paw for each group is also measured and demonstrates no difference in paw withdrawal threshold compared to controls.

EXAMPLE 5

Method for Construction of AAV-shNA Viral Production Plasmids

A BamHI fragment containing the shNA expression cassette (murine U6 promoter, shNA sequence, and Pol III terminator sequence) from a pSilencer shuttle vectors (SCN9A-specific sequences selected from SEQ ID NOs. 1-60) is recovered, blunted with T4 DNA polymerase, and subcloned into an AAV1/2 expression vector (deprAVE™; GeneDetect.com Ltd, Bradenton, Fla.). In the final viral expression vector (for virus production), the U6 promoter drives the expression of the shNA and the Woodchuck enhancer/chicken β-actin promoter drives the expression of the enhanced green fluorescent protein (WPRE/CAG-eGFP). These expression cassettes are flanked by viral inverted terminal repeats (ITR). The Woodchuck post-transcriptional regulatory element (WPRE) and the presence of a bovine growth hormone (BGH) polyadenlyation sequence ensure high transcription following cellular transduction.

Initially, cellular transduction of the viral constructs is evaluated in vitro. Individual wells of a 6-well plate containing PC12 cells at 60-70% confluency were incubated for 48 hours with $1 \times 10^{10}$ genomic particles of AAV-SCN9A sequences (at least one of SEQ ID NOs. 1-60) or were treated with a control virus (AAV vector comprising SEQ ID NO. mm55). Cellular transductions were carried out in Gibco DMEM high glucose media containing 2% fetal bovine serum for two hours before the media was supplemented with additional fetal bovine serum (10% final concentration). AAV-SCN9A virus treated cells are positive for GFP fluorescence and show reduced levels of SCN9A expression while control virus treated cells (AAV-mm55) are positive for GFP but maintain normal levels of SCN9A expression compared to non-transduced PC12 cells.

In order to optimize in vivo studies using the above described technologies, the AAV-SCN9A virus, containing SEQ ID NOs: 1-60, was used to evaluate in vivo cellular transduction. Transduction is measured in Sprague Dawley rats by the formalin test as described in Example 2 and by brightfield and fluorescent image analysis.

It also is to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a sequence" or "a shNA" is a reference to one or more sequences or shNAs and includes equivalents thereof known to those skilled in the art and so forth.

Unless defined otherwise, all technical terms used herein have the same meanings as commonly understood by one of ordinary skill in the art to which this invention belongs. Specific methods, devices, and materials are described, although any methods and materials similar or equivalent to those described herein can be used in the practice or testing of the present invention.

We claim:

1. A method of treating pain comprising:

administering to a mammal in pain a pharmaceutical composition comprising at least one isolated nucleic acid molecule of about 19 to about 25 contiguous nucleotides comprising a sequence set forth in SEQ ID NO. 55 that is complementary to or identical to a target sequence of about 19 to about 25 contiguous nucleotides in SCN9A mRNA wherein said isolated nucleic acid molecule is a siRNA molecule;

introducing the siRNA molecule into a cell body of a dorsal root ganglion; and suppressing the expression and/or function of $Na_v1.7$ channels in the dorsal root ganglion.

2. A method according to claim 1 wherein said isolated nucleic acid molecule is administered through a catheter and drug pump, via a controlled release polymer formulation or both.

3. A method according to claim 1 wherein said isolated nucleic acid molecule is in shRNA format and is delivered via a viral vector or a non-viral vector.

4. The method according to claim 1 wherein said isolated nucleic acid comprises a sense RNA strand and an antisense RNA strand, wherein said antisense RNA strand is complementary to said target sequence and said sense RNA strand is greater than 80% identical to said target sequence.

5. The method according to claim 4 wherein said sense and said antisense RNA strands are covalently linked by a single-stranded hairpin.

* * * * *

UNITED STATES PATENT AND TRADEMARK OFFICE
CERTIFICATE OF CORRECTION

| | | |
|---|---|---|
| PATENT NO. | : 8,183,221 B2 | Page 1 of 1 |
| APPLICATION NO. | : 12/676596 | |
| DATED | : May 22, 2012 | |
| INVENTOR(S) | : Thakker et al. | |

It is certified that error appears in the above-identified patent and that said Letters Patent is hereby corrected as shown below:

On Page 2, in Field (56), under "OTHER PUBLICATIONS", in Column 2, Line 8, delete "(Feb. 2005." and insert -- (Feb. 2005). --, therefor.

In Column 36, Line 9, in Claim 2, delete "A" and insert -- The --, therefor.

In Column 36, Line 13, in Claim 3, delete "A" and insert -- The --, therefor.

Signed and Sealed this
Twentieth Day of November, 2012

David J. Kappos
*Director of the United States Patent and Trademark Office*